United States Patent [19]
Bombardelli et al.

[11] Patent Number: 5,679,358
[45] Date of Patent: Oct. 21, 1997

[54] FORMULATIONS CONTAINING ESCULOSIDE AND THE USE THEREOF IN THE PHARMACEUTICAL AND COSMETIC FIELDS

[75] Inventors: Ezio Bombardelli; Aldo Cristoni; Paolo Morazzoni, all of Milan, Italy

[73] Assignee: Indena S.A., Milan, Italy

[21] Appl. No.: 498,868

[22] Filed: Jul. 6, 1995

[30] Foreign Application Priority Data

Jul. 12, 1994 [IT] Italy ................. MI94A1446

[51] Int. Cl.⁶ ......................................... A61K 35/78
[52] U.S. Cl. .............................. 424/401; 424/195.1
[58] Field of Search ................... 424/195.1, 401; 514/783, 860, 929

[56] References Cited

U.S. PATENT DOCUMENTS

| | | | |
|---|---|---|---|
| 3,609,137 | 9/1971 | Menssen et al. | 536/4.4 |
| 4,925,871 | 5/1990 | Gabetta et al. | 514/453 |
| 5,080,901 | 1/1992 | Hangay et al. | 424/195.1 |
| 5,126,331 | 6/1992 | Gazzani | 514/44 |
| 5,176,919 | 1/1993 | Curri et al. | 424/450 |
| 5,194,259 | 3/1993 | Soudant et al. | 424/401 |
| 5,376,371 | 12/1994 | Bombardelli | 424/195.1 |
| 5,466,452 | 11/1995 | Whittle | 424/195.1 |

*Primary Examiner*—Melvyn I. Marquis
*Assistant Examiner*—Robert H. Harrison
*Attorney, Agent, or Firm*—Pennie & Edmonds

[57] ABSTRACT

The present invention relates to the use of esculoside alone or in combination with adenylate cyclase stimulators, such as forskolin or *Salvia miltiorrhiza* diterpenes and/or with phosphodiesterase inhibitors, such as apigenine-skeleton dimeric flavones, in topical formulations for the treatment of peripheral vasculopathies related to an impaired peripheral microcirculation, cellulitis or unesthetisms connected with a deposit of superfluous fat. For the reduction of the deposits of superfluous fat of any origin, the above mentioned products are advantageously also combined with caffeine, theophylline and derivatives thereof.

14 Claims, 1 Drawing Sheet $* p < 0.05 \quad ** p < 0.01$

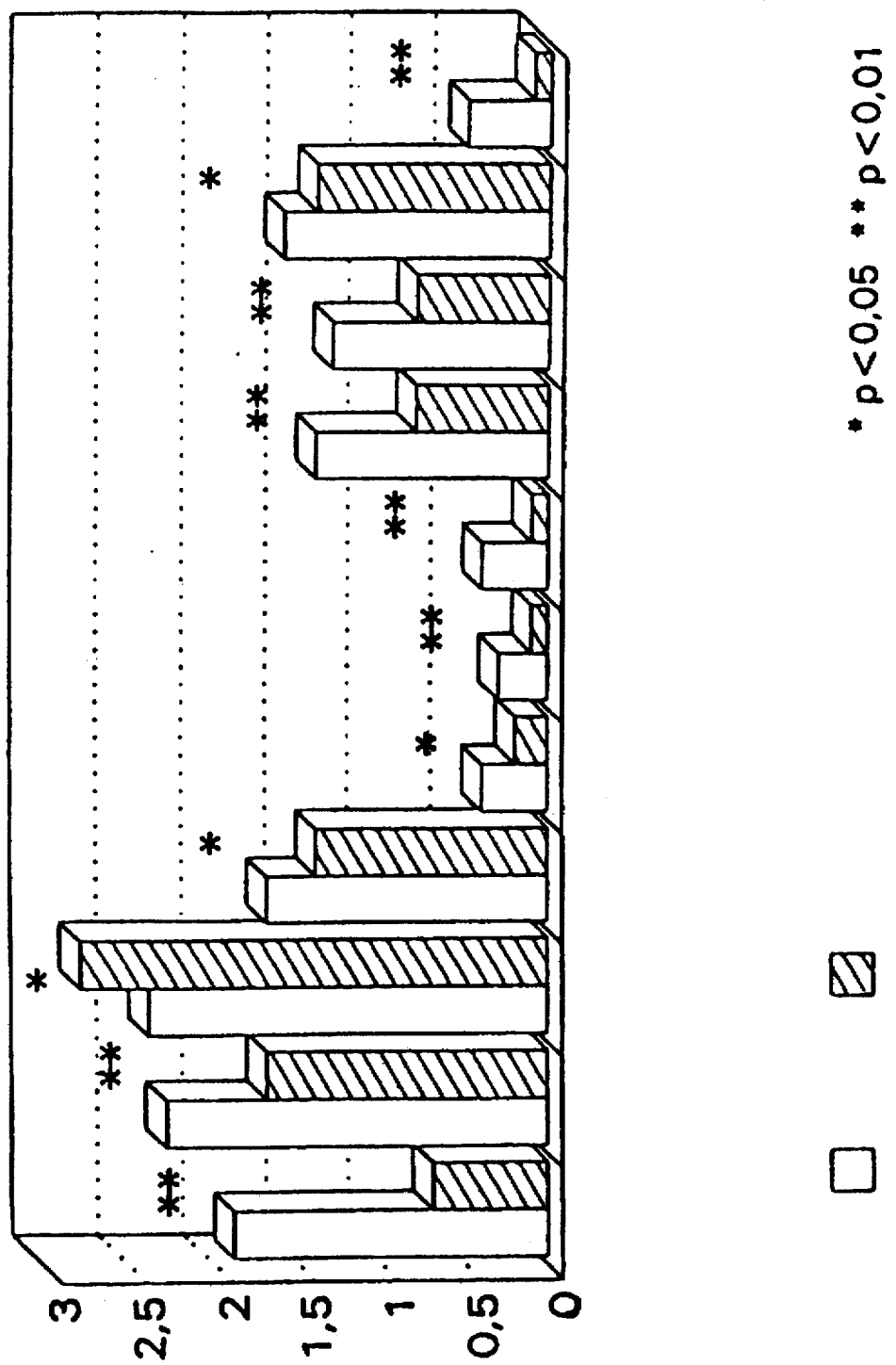
Fig.1  * p<0,05  ** p<0,01

5,679,358

FORMULATIONS CONTAINING ESCULOSIDE AND THE USE THEREOF IN THE PHARMACEUTICAL AND COSMETIC FIELDS

TECHNICAL FIELD

The present invention relates to formulations containing esculoside alone or in combination with adenylate cyclase stimulators, such as forskolin or *Salvia miltiorrhiza* direrpenes and/or phosphodiesterase inhibitors such as apigenin-skeleton dimeric flavones, for the topical use in the treatment of peripheral vasculopathies related to an impaired peripheral microcirculation; Moreover, the invention relates to the use of esculoside alone or in combination with the cited adenylate cyclase stimulators and/or with the cited phosphodiesterase inhibitors in the treatment of cellulitis or unesthetisms connected with the deposit of superfluous fat. For the latter aspect, the above mentioned products can be mixed with caffeine, theophylline, pentoxifylline.

The invention also relates to the use of esculoside alone or in combination with adenylate cyclase stimulators, such as forskolin or *Salvia miltiorrhiza* direrpenes and/or phosphodiesterase inhibitors such as apigenin-skeleton dimeric flavones for the preparation of the above cited formulations.

BACKGROUND OF THE INVENTION

A variety of conditions related to impaired peripheral microcirculation and chronic venous deficiency, including cellulitis, cellulitis like derm-hypoderm panniculopathies and stretch marks, deposits of superfluous fat, such as unesthetisms following a forced diet, Raynaud's disease, acrocyanosis, and cold induced vasospasm, have long resisted treatment. All of these conditions would respond favorably to an increase in blood flow. Therefore, a need exists for a treatment that will provide increased arterial blood flow and capillary density to improve district microcirculation.

SUMMARY OF THE INVENTION

The present invention relates to a method of treatment for peripheral vasculopathies related to an impaired peripheral microcirculation, of cellulitis, and of unesthetisms related to a deposit of superfluous fat, wherein a pharmaceutical or cosmetic formulation containing therapeutically effective amounts of esculoside alone or combined with a co-agent of at least one of an adenylate cyclase stimulator, a phosphodiesterase inhibitor, a lipolytic agent, or a mixture thereof, is applied topically to a patient or a subject in need of such treatment. Preferably, the esculoside is present in an amount of about 0.5 to 3%, while one or more of the co-agents are each present in an amount of about 0.1 to 1%. The esculoside is generally included in the formulation in an amount which is greater than that of the co-agent or the total amount of the co-agents. In this regard, a weight ratio of greater than 1:1 up to about 6:1 has been found to be particularly advantageous, as shown by the Examples. The balance of the formulation would include one or more pharmaceutically acceptable carriers so that a topical cream, gel, ointment or lotion may be prepared to facilitate administration of the active ingredients to the subject.

BRIEF DESCRIPTION OF THE DRAWING

FIG. 1 is a chart showing the results of a treatment of cellulitis according to the present invention.

DETAILED DESCRIPTION OF THE INVENTION

Esculoside is a glucosidated coumarin extracted from the fruit pericarp and from the bark of *Aesculus hippocastanum*. Such a product has been used for a long time in the treatment of pathological conditions connected with an impaired permeability and capillary fragility, and it is still used for the topical or systemic administration in the treatment of venous stasis vasculopathies, hemorrhoids and as a decongestionant in ophthalmology. Now it has surprisingly been found that esculoside, alone or in combination with the above cited products, when topically administered increases both arterial blood flow (activity on myocytes of arteries and precapillary arterioles increasing the sphygmicity thereof) in the administration area, and the number of perfused capillaries, thus improving the superficial and deep circulations. This phenomenon was measured by means of non-invasive techniques, such as infrared photopulsoplethysmography, laser Doppler flowmetry and computerized videocapillaroscopy. The first two techniques provide evidence of the vasomotility of the arteries and precapillary arterioles, whereas the latter provides an evaluation of the changes in the capillary bed and the district angiotectonic. After recording the basal data, a placebo formulation or the formulation containing the active ingredient or the active principals are applied on the body area treated. Usually two symmetric body parts are used, randomizing the test. Immediately after the treatment, the treated areas are checked with a video-capillaroscope (Scopeman-Moritex Video Imaging System, Alfa Strumenti, Milan) fitted with a halogen-light optical probe with 50 to 400×magnifications, measuring the capillary density (number of blood-perfused capillaries per surface unit) and evaluating the space orientation of the capillaries and the morphology thereof. The instrumentation was fitted with a videocamera for continuously recording the biomicroscopical images to allow the quantification of any changes during the elaboration phase. Twenty minutes after the treatment with esculoside alone or in combination with the products mentioned above, such as *Ginkgo biloba* dimeric flavones or amentoflavone, to cite the most important compounds, an increase in capillary density up to 200–300% took place, compared with the basal and placebo-treated control. The action of esculoside in concentrations ranging from 0.5 to 3%, evaluated as described above, lasts from one to three hours. Videocapillaroscopy, as mentioned above, allows an evaluation of skin microangiotectonic, providing evidence of the number of perfused capillaries as well as the orientation in space and stratification thereof.

It has surprisingly been found, and it is a part of the present invention, that, when formulations containing esculoside alone or in combination with a co-agent of a compound having adenylate cyclase stimulating activity or antiphosphodiesterase activity, and optionally also other lipolytic agents such as caffeine, theophylline, pentoxifylline, are administered to the area affected with disorders due to chronic venous deficiency, such as cellulitis, or on deposits of superfluous fat such as the unesthetisms following a forced diet, a marked decrease in the pathology occurs thanks to the improvement of district microcirculation due to esculoside and to the lipolytic effect of the other components. The administrations are performed for times ranging from a few days to some months, usually three months, depending on the severity of the pathology or the unesthetism.

As far as the vascular system is concerned, esculoside alone or in combination with antiphosphodiesterase agents or adenylate cyclase stimulating agents can be used in chronic venous insufficiency, in Raynaud's disease and in acrocyanosis, as well as against cold-induced vasospasm, particularly for microcirculation in the fingers and toes. The higher blood flow to the areas treated with the active ingredients also improve skin early ageing, particularly face and neck skin, cellulitis-like derm-hypoderm panniculopathies and stretch marks (striae distensae) Moreover, the higher blood supply also acts favorably on non-glabrous skin, such as scalp, and is useful in the treatment of the primitive and secondary alopecias.

In the cosmetic fields, the main uses of the products object of invention relate the ageing of the skin and cellulitis, which affects a high percentage of the population in the industrialized Countries.

By way of example of the above described uses, 20 patients suffering from chronic venous insufficiency (Stage I) were subdivided into two groups and treated with a formulation containing 1.5% esculoside or with placebo for 3 months, twice a day, administering the product from the trocanterian area to the ankle.

The patients, before the long-term treatment, were checked to evaluate their response capability by an acute test by means of videocapillaroscopic measurement of the increase in cutaneous microcirculation. The capillary density in the group treated with placebo, measured 20 minutes after the treatment, was 8.6±2.2%, whereas in the group treated with esculoside it was 18.6±3.1%, with p<0.01 calculated by Student test.

The observed symptoms and their intensity, evaluated according to a severity score ranging from 0 to 4, are reported in the following tables:

to the ankle for three months with a formulation containing 1.5% esculoside, 0.3% of *Salvia miltiorrhiza* extract (this extract containing 15% tanshinone A2), 0.4% *Ginkgo biloba* dimeric flavones (prepared according to Indena Patent EP 0360556) and 0.2% theophylline. In these subjects, the observed parameters dramatically changed, as shown by the data reported in FIG. 1.

In another test, a group of 20 subjects affected with fibrosclerotic panniculopathy of the trochanterian area with a deposit of superfluous fat was treated for 2 months with a formulation containing 1.5% esculoside, 0.3% *Salvia miltiorrhiza* extracts of and 1% pentoxifylline. The main control parameter was the reduction of the deposit of superfluous fat, therefore the diameter of the trochanterian area was measured, and was surprisingly decreased by 2.6±0.2 cm.

EXAMPLES

A number of other tests were carried out changing the composition and the components ratios or the nature of the components, for the treatment of the above cited pathologies and unesthetisms. The formulations according to the invention contain, besides the above mentioned active principles, the conventional carriers, additives, preservatives and the like known in pharmaceutical technique, such as those reported in the following non-limiting examples.

Example I

Gel containing esculoside, *Salvia miltiorrhiza* extract and *Ginkgo biloba* dimeric flavones.

TABLE I

Evaluation of the symptoms in patients affected with venous insufficiency of the leg, before and after a 3 months-treatment with 1.5% esculoside.

| | Patient No | | | | | | | | | | | | | | | | | | | |
|---|---|---|---|---|---|---|---|---|---|---|---|---|---|---|---|---|---|---|---|---|
| Before: | 1 | | 2 | | 3 | | 4 | | 5 | | 6 | | 7 | | 8 | | 9 | | 10 | |
| After: | | 1 | | 2 | | 3 | | 4 | | 5 | | 6 | | 7 | | 8 | | 9 | | 10 |
| Leg heaviness | 0 | 0 | 3 | 2 | 2 | 1 | 3 | 1 | 2 | 0 | 3 | 1 | 2 | 1 | 3 | 2 | 0 | 0 | 3 | 1 |
| Oedema | 0 | 0 | 2 | 1 | 3 | 1 | 2 | 0 | 1 | 0 | 3 | 2 | 1 | 0 | 2 | 1 | 1 | 0 | 3 | 1 |
| Paresthesia | 1 | 0 | 2 | 0 | 0 | 0 | 1 | 0 | 3 | 1 | 2 | 0 | 0 | 0 | 2 | 1 | 1 | 0 | 1 | 0 |
| Diurnal cramps | 0 | 0 | 4 | 2 | 2 | 0 | 3 | 1 | 0 | 0 | 2 | 0 | 3 | 1 | 2 | 0 | 0 | 0 | 0 | 0 |
| Nocturnal cramps | 0 | 0 | 3 | 1 | 1 | 0 | 3 | 1 | 0 | 0 | 1 | 0 | 2 | 0 | 1 | 1 | 0 | 0 | 0 | 0 |
| Venous telangiectasia | 1 | 1 | 1 | 1 | 2 | 2 | 1 | 1 | 2 | 2 | 3 | 3 | 1 | 1 | 3 | 3 | 1 | 1 | 0 | 0 |
| Varices | 0 | 0 | 0 | 0 | 0 | 0 | 0 | 0 | 1 | 1 | 1 | 1 | 0 | 0 | 0 | 0 | 0 | 0 | 0 | 0 |
| Nervous legs | 0 | 0 | 4 | 1 | 3 | 0 | 4 | 2 | 3 | 1 | 4 | 2 | 2 | 0 | 3 | 0 | 1 | 0 | 3 | 1 |
| Cold feet | 3 | 2 | 4 | 1 | 4 | 2 | 4 | 1 | 4 | 2 | 3 | 1 | 4 | 2 | 4 | 2 | 4 | 2 | 3 | 1 |

| Symptoms | Before | After | P< |
|---|---|---|---|
| Leg heaviness | 2.1 ± 0.38 | 0.9 ± 0.23 | P < 0.01 |
| Oedema | 1.8 ± 0.33 | 0.6 ± 0.22 | P < 0.01 |
| Paresthesia | 1.5 ± 0.34 | 0.3 ± 0.15 | P < 0.01 |
| Diurnal cramps | 1.6 ± 0.48 | 0.4 ± 0.22 | P < 0.01 |
| Nocturnal cramps | 1.1 ± 0.38 | 0.3 ± 0.15 | P < 0.05 |
| Venous Telangiectasia | 1.5 ± 0.31 | 1.5 ± 0.31 | N.S. |
| Varices | 0.2 ± 0.13 | 0.2 ± 0.13 | N.S. |
| Nervous legs | 2.7 ± 0.42 | 0.7 ± 0.26 | P < 0.01 |
| Cold feet | 3.7 ± 0.15 | 1.6 ± 0.16 | P < 0.01 |

In thigh cellulitis due to chronic venous insufficiency, a group of 20 subjects was treated from the trocanterian area 100 g of gel contain:

| | |
|---|---|
| *Salvia miltiorrhiza* extract | 0.30 g |
| Esculoside | 1.50 g |
| *Ginkgo biloba* dimeric flavones | 0.50 g |
| Hydrogenated castor oil 40(OE) (Cremophor RH40 - BASF) | 1.00 g |
| Propylene glycol | 1.50 g |
| Preservatives | 0.10 g |
| Hydroxyethyl cellulose (Natrosol 250 HHX - Aqualon) | 3.00 g |
| Purified water | q.s. to 100 g |

Example II

Alcoholic fluid gel containing *Salvia miltiorrhiza* extract and caffeine.

100 g of gel contain:

| | |
|---|---|
| *Salvia miltiorrhiza* extract | 0.25 g |
| Esculoside | 1.50 g |
| Caffeine | 0.50 g |
| Hydrogenated castor oil 40(OE) (Cremophor RH40 - BASF) | 5.00 g |
| Propylene glycol | 3.00 g |
| Carbomer 940 (Carbopol 980 - Goodrich) | 1.00 g |
| Ethanol | 45.00 g |
| Phosphatidylcholine (Phospholipon 90 - Natterman) | 0.70 g |
| Gliceryl 6(OE)Caprilate/Caprinate (Softigen 767) | 15.00 g |
| Preservatives | 0.40 g |
| Butylhydroxytoluene | 0.05 g |
| α-Tocopherol | 0.20 g |
| Ascorbic acid | 0.30 g |
| Dimethicone copolyol (SF 1188 - General Electric) | 2.00 g |
| 10% Triethanolamine sol. | 5.00 g |
| Depurated water | q.s. to 100 g |

Example III

Cream containing esculoside, *Salvia miltiorrhiza* extract and extract of Cola nut titrated in caffeine-like alkaloids.
100 g of cream contain:

| | |
|---|---|
| *Salvia miltiorrhiza* extract | 0.25 g |
| Esculoside | 1.50 g |
| Cola nut dry extract (14% total alkaloids) | 0.50 g |
| Hydrogenated castor oil 40(OE) (Cremophor RH40 - BASF) | 2.00 g |
| Propylene glycol | 2.00 g |
| Carbomer 934 (Carbopol 934 P - Goodrich) | 0.50 g |
| Acrylates/Alkyl $C_{10-30}$ - Acrylate crosspolymer (Carbopol 1382 - Goodrich) | 0.50 g |
| Ethanol | 15.0 g |
| Preservatives | 0.40 g |
| Cetyl Palmitate (Cutina CP - Henkel) | 8.00 g |
| Polyisoprene (Syntesqual - Vevy) | 5.00 g |
| Polysorbate 80 (Tween 80 - ICI Americans) | 2.00 g |
| α-Tocopherol | 0.20 g |
| Ascorbyl palmitate | 0.10 g |
| Hydrogenated lanolin (Lanocerina - Esperis) | 5.00 g |
| Dimethicone 350 cps (Tegiloxan 350 - Tego) | 0.50 g |
| 10% NaOH sol. | 2.40 g |
| Depurated water | q.s to 100 g |

Example IV

Lotion containing esculoside and theophylline.
100 ml of lotion contain:

| | |
|---|---|
| Esculoside | 1.00 g |
| Theophylline | 0.50 g |
| Butylhydroxytoluene | 0.10 g |
| Ethyl alcohol 50° | q.s. to 100 ml |

Example V

Gelified emulsion containing esculoside.

100 g of gelified emulsion contain:

| | |
|---|---|
| Esculoside | 1.00 g |
| Isopropyl myristate | 5.00 g |
| Preservatives | 0.40 g |
| Perfume | 0.10 g |
| Polyacrylamide, $C_{13-14}$ Isoparaffin and lauric alcohol 7(OE) (Sepigel 305 - Seppic) | 3.00 g |
| Depurated water | q.s. to 100 g |

What is claimed is:

1. A topical pharmaceutical or cosmetic composition for the treatment of peripheral vasculopathies, comprising esculoside in an amount of about 0.5% to 3%, and about 0.1 to 1% of a co-agent of at least one of an adenylate cyclase stimulator, a phosphodiesterase inhibitor, a lipolytic agent, or a mixture thereof.

2. The composition of claim 1, further comprising a carrier and wherein the esculoside is present in a weight ratio with regard to the co-agent of greater than 1:1 to about 6:1.

3. The composition of claim 1, wherein the co-agent is an adenylate cyclase stimulator of forskolin, *Salvia miltiorrhiza* diterpenes, or a mixture thereof.

4. The composition of claim 1, wherein the co-agent is a phosphodiesterase inhibitor of an apigenin-skeleton dimeric flavone.

5. The composition of claim 4, wherein the flavone is a *Ginkgo biloba* dimeric flavone or amentoflavone.

6. The composition of claim 1, wherein the co-agent is a lipolytic agent of caffeine, theophylline, pentoxifylline, or a mixture thereof.

7. The composition of claim 3, comprising about 0.25% to about 0.3% of the *Salvia miltiorrhiza* diterpene.

8. The composition of claim 5, comprising about 0.4% to about 0.5% *Ginkgo biloba* dimeric flavones.

9. A topical pharmaceutical or cosmetic composition for the treatment of peripheral vasculopathies, comprising esculoside in an amount of about 0.5% to 3%, and about 0.1 to 1% of a co-agent of at least one of an adenylate cyclase stimulator, a phosphodiesterase inhibitor, a lipolytic agent, or a mixture thereof, wherein the esculoside is present in a weight ratio with regard to the co-agent of greater than 1:1 to about 6:1.

10. The composition of claim 9, wherein the co-agent is an adenylate cyclase stimulator of forskolin, *Salvia miltiorrhiza* diterpenes, or a mixture thereof.

11. The composition of claim 9, wherein the co-agent is a phosphodiesterase inhibitor of an apigenin-skeleton dimeric flavone.

12. The composition of claim 11, wherein the flavone is a *Ginkgo biloba* dimeric flavone or amentoflavone.

13. The composition of claim 9, wherein the co-agent is a lipolytic agent of caffeine, theophylline, pentoxifylline, or a mixture thereof.

14. The composition of claim 9, further comprising a carrier, wherein the co-agent is a *Salvia miltiorrhiza* diterpene and is present in an amount of about 0.25% to about 0.3%.

* * * * *